United States Patent [19]

Roemer et al.

[11] Patent Number: 4,482,548
[45] Date of Patent: Nov. 13, 1984

[54] ANALGESIC PHARMACEUTICAL COMPOSITIONS CONTAINING 5-PHENYL-1,4-BENZO DIAZEPINE COMPOUNDS AND A METHOD OF USING SAME

[75] Inventors: Dietmar Roemer, Allschwil, Switzerland; Michael Ruhland; Horst Zeugner, both of Hanover, Fed. Rep. of Germany; Wolfgang Milkowski, Burgdorf, Fed. Rep. of Germany; Hans Liepmann, Hanover, Fed. Rep. of Germany

[73] Assignee: Kali-Chemie Pharma GmbH, Hanover, United Kingdom

[21] Appl. No.: 494,645

[22] Filed: May 16, 1983

[30] Foreign Application Priority Data

Jun. 5, 1982 [DE] Fed. Rep. of Germany ....... 3221402

[51] Int. Cl.³ ............................................. A61K 31/33
[52] U.S. Cl. .................................................. 424/244
[58] Field of Search ........................................ 424/244

[56] References Cited

U.S. PATENT DOCUMENTS 3,998,809 12/1976 Milkowski et al. .......... 260/239 BD
4,096,141 6/1978 Milkowski et al. .......... 260/239 BD

FOREIGN PATENT DOCUMENTS 826159 10/1969 Canada .

OTHER PUBLICATIONS

European Search Report.

Primary Examiner—Stanley J. Friedman
Attorney, Agent, or Firm—Schwartz, Jeffery, Schwaab, Mack, Blumenthal & Koch

[57] ABSTRACT

Highly effective analgesic pharmaceutical compositions and methods of using same are described. Said compositions contain, as analgesic agent, a 5-phenyl-1H-2,3-dihydro-1,4-benzodiazepine compound of the formula

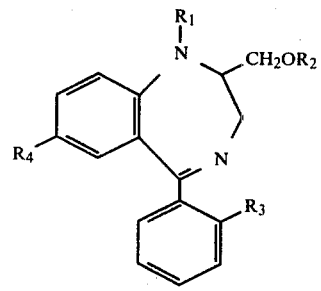

wherein
  $R_1$ indicates a substituent selected from the group consisting of hydrogen and lower alkyl,
  $R_2$ indicates a substituent selected from the group consisting of hydrogen, lower alkyl, and lower alkanoyl,
  $R_3$ indicates a substituent selected from the group consisting of hydrogen and halogen, and
  $R_4$ indicates halogen, or a physiologically compatible acid addition salt thereof.

8 Claims, No Drawings

ANALGESIC PHARMACEUTICAL COMPOSITIONS CONTAINING 5-PHENYL-1,4-BENZO DIAZEPINE COMPOUNDS AND A METHOD OF USING SAME

BACKGROUND OF THE INVENTION

The present invention relates to novel pharmaceutical compositions of high analgesic activity and more particularly to pharmaceutical compositions which contain as effective analgesic agent a 5-phenyl-1H-2,3-dihydro-1,4-benzo diazepine compound of the following FORMULA I

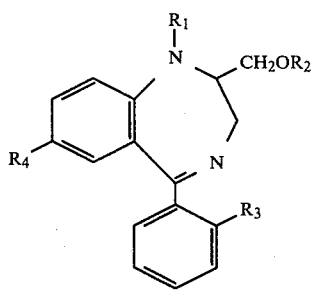

or physilogically compatible acid addition salts thereof. In said Formula I $R_1$ indicates hydrogen or lower alkyl,
$R_2$ indicates hydrogen, lower alkyl, or lower alkanoyl,
$R_3$ indicates hydrogen or halogen, and
$R_4$ indicates halogen.

The invention furthermore pertains to the method of treating humans and animals with said compounds as an analgesic agent.

The benzo diazepine compounds of Formula I used as highly effective analgesic agents in the pharmaceutical compositions according to the present invention are comprised by the 5-phenyl-1H-2,3-dihydro-1,4-benzo diazepine compounds which carry in the 2-position a substituted methyl group, as described in U.S. Pat. Nos. 3,998,809, 4,096,141, 4,098,786 and 4,244,869. Said compounds possess the central nervous system influenzing properties and more particularly possess anxiolytic and tranquilizing properties.

SUMMARY OF THE INVENTION

It is one object of the present invention to provide the medical profession with novel and valuable pharmaceutical compositions having a surprisingly high analgesic activity with an improved profile of efficacy.

Another object of the present invention is to provide a process of producing such analgesic pharmaceutical compositions.

Still another object of the present invention is to provide a simple and effective method of using the novel and highly effective pharmaceutical compositions as analgesic agents.

Other objects of the present invention and advantageous features thereof will become apparent as the description proceeds.

In principle the pharmaceutical compositions according to the present invention comprise as highly effective analgesic agent and component 5-phenyl-1H-2,3-dihydro-1,4-benzo diazepine compounds of the following Formula I

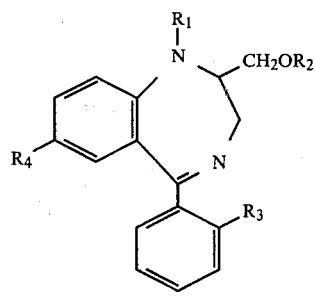

In said Formula $R_1$ indicates hydrogen or lower alkyl,
$R_2$ indicates hydrogen, lower alkyl, or lower alkanoyl,
$R_3$ indicates hydrogen or halogen, and
$R_4$ indicates halogen.

Preferably the lower alkyl or lower alkanoyl substituents $R_1$ and $R_2$ are lower alkyl or lower alkanoyl groups with 1 to 4 carbon atoms. More advantageously the substituent $R_1$ represents hydrogen, methyl, or ethyl. The substituent $R_2$ is preferably hydrogen or a lower alkyl group, more particularly an alkyl group with 1 to 3 carbon atoms and more advantageously the methyl group. The substituent $R_3$ represents preferably halogen and more particularly fluorine, chlorine, or bromine, and most advantageously chlorine. The halogen substituent $R_4$ represents more specifically chlorine or bromine. The preferred substituent $R_4$ is bromine. The physiologically compatible acid addition salts of these compounds can also be used. Especially useful has proved 1-methyl-7-bromo-2-methoxy methyl-5-(2-chloro phenyl)-1H-2,3-dihydro-1,4-benzo diazepine and its physiologically compatible acid addition salts.

Surprisingly it has been found that the compounds of Formula I as given hereinabove are favorably characterized by a novel and highly advantageous profile of activity. They possess, in addition to their above-mentioned central nervous system controlling activity, also a highly pronounced analgesic activity component. The analgesic activity of the compounds of Formula I is exhibited surprisingly already at a dosage range at which sedative and muscle relaxing effects cannot yet be observed.

Due to said favorable profile of activity and their excellent compatibility, the compounds of Formula I have proved to be especially suitable for treating and alleviating pain and for the preparation of valuable analgesic pharmaceutical compositions.

The analgesic activity and the satisfactory compatibility of the compounds of Formula I according to the present invention and more particularly the favorable ratio of the analgesic doses to the doses at which undesired sedative and muscle relaxing effects are observed, can be demonstrated by standard pharmacological tests on animals. Such tests, for instance, compare the pain allaying effect of the test compound in the arthritis pain test with the sedative and muscle relaxing effects which impair the normal activity of rats.

DETAILED DESCRIPTION OF PREFERRED EMBODIMENTS

DESCRIPTION OF THE PHARMACOLOGICAL TEST METHODS

1. Arthritis pain test on rats.

Male rats of the OFA strain, weighing between 160 g. and 180 g. are anesthetized by intraperitoneal administration of 20 mg./kg. of Pentobarbital Sodium. 0.1 ml. of a suspension of 0.6 mg. of Mycobacterium Smegmae (SI043) in paraffin oil are injected intracutaneously into the left hind paw of the rats. Fourteen days thereafter, when a pronounced secondary arthritis has developed especially in the right hind paw of the rats, the effects of the test compounds are investigated. For this purpose a control measurement is carried out thirty minutes before administration of the compound to be tested by deflecting three times the ankle joints of the right hind paws of the test animals and counting the number of distress sounds emitted by them. Rats which do not react are eliminated from the test. The ankle joint deflecting procedure is repeated three hours after oral administration of the compounds to be tested. Animals which emit distress sounds either only once or not at all are considered as being protected against pain. The dosage by which protection against pain is achieved in 50% of the treated animals is designated as the effective dosage $ED_{50}$.

2. Determination of the inhibition of the locomotion exploratory activity according to the method described by Janssen in "Psychopharmakologie", vol. 1 (1961), pages 141–146.

The compound to be tested is orally administered in the form of a suspension in 2% Tylose solution to male rats of the Sprague-Dawley type one hour before starting the test. Six pairs of rats are used for each dosage to be administered. Each pair of rats is then placed into an environment which is entirely unknown to them. The locomotor activity of said rats with respect to the exploration and inquisitiveness phase within the first thirty seconds is observed and recorded by two observers. The observed activity is evaluated according to a point system. According to said system the highest possible number of points for six pairs of rats amounts to 18 points. That dosage which corresponds to 9 points for six pairs of rats is designated as $ED_{50}$.

In the following Table there are compared the values obtained according to the hereinabove described test methods for two compounds according to the present invention with the values obtained by using the drug Diazepam as comparative compound. The tested compound No. 1 is the 1-methyl-7-bromo-2-methoxy methyl-5-(2-chloro phenyl)-1H-2,3-dihydro-1,4-benzo diazepine in the form of its hydrochloride, and the tested compound No. 2 is the 1-methyl-7-chloro-2-methoxy methyl-5-(2-chloro phenyl)-1H-2,3-dihydro-1,4-benzo diazepine, also in the form of its hydrochloride, while the comparison compound is the 7-chloro-1-methyl-5-phenyl-1,3-dihydro-2H-1,4-benzo diazepin-2-one which is known under the generic name Diazepam.

TABLE

| Test compound | Suppression of the arthritis pain in rats $ED_{50}$ mg./kg. p.o. | Suppression of the locomotor exploration activity on rats $ED_{50}$ mg./kg. p.o. | Acute toxicity on mice $ED_{50}$ mg./kg. p.o. |
|---|---|---|---|
| Compound No. 1 | 4.8 | 56.2 | 2390 |
| Compound No. 2 | 10.0 | 55.5 | 1470 |
| Diazepam | 6.2 | 11.5 | 825 |

These test results clearly show that the tested compounds of Formula I have a satisfactory analgesic activity, but that, in contrast to Diazepam, they negatively affect the normal locomotor behavior with respect to exploration and inquisitiveness at considerably higher dosages only.

The compounds of Formula I can be used, as stated above, in the form of their free bases or of their physiologically compatible acid addition salts as active agents in the treatment of pain and for the preparation of analgesically active pharmaceutical compositions. Suitable physiologically acceptable acid addition salts of the compounds of Formula I are salts with inorganic acids, such as hydrochloric acid, hydrobromic acid, sulfuric acid, or phosphoric acid, or salts with organic acids, such as, for instance, salts with acetic acid, maleic acid, fumaric acid, benzoic acid, methane sulfonic acid, cyclohexyl amino sulfonic acid, lactic acid, tartaric acid, or phenyl acetic acid.

The doses to be administered can differ individually. They vary, of course, depending on the type of condition to be treated, on the compound used, and on the mode of administration. For instance, parenterally administrable compositions will contain, in general, a smaller amount of active agent than orally administrable preparations. As a rule pharmaceutical compositions containing between about 0.25 mg. and about 25.0 mg. and more particularly between 5.0 mg. and 15.0 mg. of the active agent for each single dose (corresponding to a dosage of 0.0035 to 0.35 more particularly of 0.07–0.25 mg/kg bodyweight) have proved to yield satisfactory results in the treatment of humans and larger mammals.

The compounds of Formula I can be contained, according to the present invention, in liquid or solid pharmaceutical compositions together with conventional pharmaceutical excipients and/or binding agents. As examples of solid preparations there may be mentioned orally administrable compositions such as tablets, capsules powders, granules, or dragees as well as suppositories. Solid compositions may contain inorganic and/or organic binder materials as they are conventionally used in pharmaceutical preparations, such as, for instance, talc, lactose, or starch. In addition thereto the preparations may contain conventional pharmaceutical excipients, for instance lubricants, such as magnesium stearate or tablet disintegrating agents. Liquid compositions such as solutions, suspensions, or emulsions may contain the usual diluents such as water, oils, vaseline, and/or dispersing agents, such as poly-oxy ethylene glycol and the like. Further additional excipients may be added such as, for instance, preservatives, stabilizing agents, agents improving the taste of the composition, and the like.

If desired, solid pharmaceutical preparations which are to be orally administered, may also contain suitable agents which retard liberation and resorption of the active agents, such as, for instance, polyvinyl acetate, copolymers of acrylates or methacrylates, higher fatty alcohols, and other wax-like compounds.

The active agents can be mixed and compounded with the pharmaceutical excipients and/or binders in a manner known per se. In order to produce solid pharmaceutical preparations the active agents can be mixed, for instance, with the pharmaceutical excipients and/or binders in a conventional manner and the resulting wet or dry mixtures can then be granulated. Depending on the nature and type of the additives employed, it is also possible to produce a powder which can directly be tableted by simply mixing and pulverizing the ingredients. The resulting granulate or powder can directly be filled into capsules or they can be compressed in a manner known per se to form tablet cores. If desired, such cores can be coated so as to form dragees and the like preparations in a manner known per se.

As stated above, the compounds of Formula I are known from, or can be prepared according to the methods described in the above-cited U.S. patents and/or in U.S. application Ser. No. 422,297 filed Sept. 23, 1982. The disclosures of these documents are hereby incorporated by reference.

More particularly acyl diamino compounds of Formula II

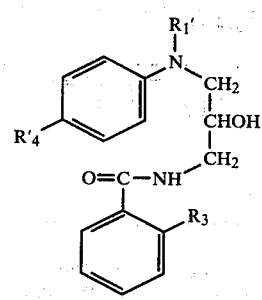

II in which
the substituent R₃ indicates hydrogen or halogen,
the substituent R₄' indicates halogen or hydrogen, and
the substituent R₁' indicates lower alkyl,
as they are obtained by acylation of the corresponding 2-hydroxy-1,4-diamino propane compounds, are subjected to cyclization in a manner known per se by reaction with phosphorus oxychloride. In this manner, a mixture of isomeric compounds of Formula IIIa and IIIb are obtained:

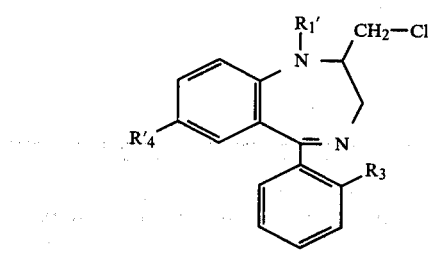

IIIa

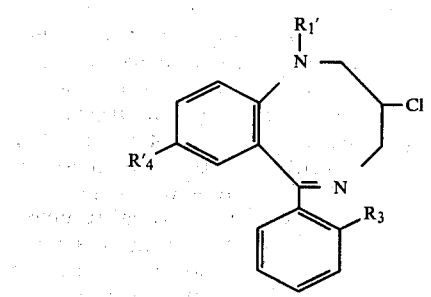

IIIb

In said Formulas the subtituents R₁', R₃, and R₄' indicate the same substituents as given hereinabove.

Thereupon, the mixture of compounds of Formulas IIIa and IIIb is converted in a manner known per se into the alcohols or ethers of Formula I by reaction with a nucleophilic reagent, such as an alkali metal hydroxide or an alkali metal alcoholate. In the resulting alcohols or ethers of Formula I the substituent R₂ indicates hydrogen or lower alkyl. If desired, the alcohols of Formula I can subsequently be converted in a manner known per se into the corresponding esters in which the substituent R₂ indicates lower alkanoyl.

In case the substituent R₄' represents hydrogen, the compounds of Formulas IIIa and IIIb can be converted in a manner known per se into compounds in which said substituent is chlorine or bromine, for instance, by a treatment with chloro succinimide or with bromo succinimide. Likewise, if the substituent R₄ in the final products of Formula I is hydrogen, it can subsequently be converted, if desired, into chlorine or bromine.

In order to produce compounds of Formula I in which R₁ indicates hydrogen, compounds of Formula IIIa in which R₁' indicates methyl and R₄' indicates halogen are preferably demethylated by a treatment with hydrogen iodide and the demethylated compounds are then subjected to ring closure by treating them with a strong base, for instance, with an alkali metal alcoholate or hydride in an inert solvent at increased temperature. In this manner compounds of Formula IV

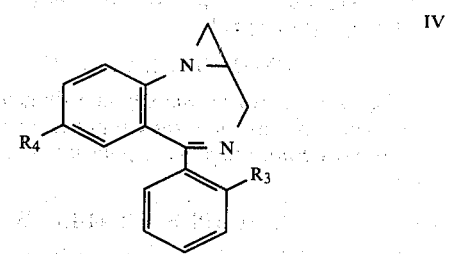

IV in which the substituents R₃ and R₄ indicate the substituents given for the compounds of Formula I, are obtained. The resulting compound of Formula IV is then reacted with a lower alcohol or a lower aliphatic carboxylic acid in the presence of a Lewis acid to yield compounds of Formula Ia Ia In said compounds of Formula Ia the substituents R₃ and R₄ are the same substituents as designated for the compounds of Formula I while the substituent R₂' indicates lower alkyl or lower alkanoyl. If desired, the resulting esters of Formula Ia, in which the substituent R₂' indicates lower alkanoyl, can be hydrolyzed to the corresponding alcohols of Formula I, in which the substituent R₂ indicates hydrogen.

The following examples serve to illustrate the present invention and more particularly the production of pharmaceutical compositions according to the present invention without, however, being limited thereto.

EXAMPLE 1: TABLETS

Tablets of the following composition per tablet are produced:

| | |
|---|---|
| 1-Methyl-7-bromo-2-methoxy methyl-5-(chloro phenyl)-1H—2,3-dihydro-1,4-benzo diazepine hydrochloride | 10 mg. |
| corn starch | 60 mg. |
| lactose | 145 mg. |
| gelatin (10% aqueous solution) | 6 mg. |

The active agent, cornstarch, and lactose are mixed with the 10% aqueous gelatin solution to yield a thick paste. The resulting paste is comminuted. The thus produced granular mass is placed on a suitable plate and is dried at 45° C. The dried granular mixture is then passed through a crusher and is mixed in a mixer with the following additional excipients:

| | |
|---|---|
| Talc | 5 mg. |
| magnesium stearate | 5 mg. |
| corn starch | 9 mg. |

The resulting mixture is then compressed to tablets, each weighing 240 mg. and containing 10 mg. of the active analgesic agent.

EXAMPLE 2: DRAGEES

The tablet cores produced according to Example 1 are coated in a manner known per se to form dragees and the resulting dragees are polished by means of bees wax.

EXAMPLE 3: TABLETS

Tablets of the following composition per tablet are produced:

| | |
|---|---|
| 7-Bromo-2-hydroxy methyl-5-(2-chloro phenyl)-1H—2,3-dihydro-1,4-benzo diazepine hydrochloride | 5 mg. |
| corn starch | 60 mg. |
| lactose | 150 mg. |
| gelatin (10% aqueous solution) | 6 mg. |
| magnesium stearate | 5 mg. |
| cornstarch | 9 mg. |

Said ingredients are worked up to tablets as described in Example 1, each tablet weighing 240 mg.

EXAMPLE 4: CAPSULES

Capsules of the following composition per capsule are produced:

| | |
|---|---|
| 1-Methyl-7-bromo-2-methoxy methyl-5-(2-chloro phenyl)-1H—2,3-dihydro-1,4-benzo diazepine | 10 mg. |
| mannite | 175 mg. |
| talc | 12 mg. |
| colloidal silica | 1 mg. |
| magnesium stearate | 2 mg. |
| | 200 mg. |

The sieved ingredients are intimately mixed with each other and the resulting powder is filled in capsules, each capsule containing 200 mg. of the powder.

EXAMPLE 5: SUPPOSITORIES

Suppositories of the following composition per suppository are produced:

| | |
|---|---|
| 1-Methyl-7-chloro-2-methoxy methyl-5-(2-chloro phenyl)-1H—2,3-dihydro-1,4-benzo diazepine hydrochloride | 25 mg. |
| cocoa butter | 1975 mg. |

The active compound and the finely triturated suppository base are intimately mixed with each other. The mixture is then molten. The molten mixture is homogenized by stirring and is poured into suppository molds. In this manner suppositories weighing 2 g. and containing 25 mg. of the analgesic compound are produced.

EXAMPLE 6: INJECTABLE SOLUTION

An injectable solution of the following composition per milliliter is produced:

| | |
|---|---|
| 1-Methyl-7-bromo-2-methoxy methyl-5-(2-chloro phenyl)-1H—2,3-dihydro-1,4-benzo diazepine | 5 mg. |
| dimethyl acetamide | 10 mg. |
| propylene glycol | 50 mg. |
| benzyl alcohol | 1.4 mg. |
| ethanol | 10 mg. |
| water pro injectione | ad 1 ml. |

The active compound is dissolved in dimethyl acetamide. Propylene glycol, benzyl alcohol, ethanol, and water are then admixed to said solution. The resulting mixture is filtered through a candle filter. The filtrate is filled into suitable ampoules. The ampoules are sealed and sterilized.

EXAMPLE 7: DROPS

A solution to be applied in the form of drops of the following composition per milliliter is produced:

| | |
|---|---|
| 1-Methyl-7-bromo-2-methoxy methyl-5-(chloro phenyl)-1H—2,3-dihydro-1,4-benzo diazepine hydrochloride | 10 mg. |
| ethanol | 300 mg. |
| 1,2-propanediol | 300 mg. |
| sorbitol | 350 mg. |
| N sodium hydroxide solution to adjust the pH-value to a pH of 6.5 | q.s. |
| taste improving agents such as orange flavor | q.s. |
| demineralized water | ad 1 ml. |

The active compound is dissolved in the liquid ingredients and the resulting solution is filled into drop bottles.

Of course, many changes and variations in the composition of the pharmaceutical preparations according to the present invention, in the active compounds used, in the pharmaceutical excipients, binding agents, preservatives, emulsifying agents, disintegrating agents, flavoring agents, coating agents, resorption retarding agents, and the like to be used in order to produce the desired pharmaceutical compositions according to the present invention, in the mode of administration and the amounts of the active compounds to be administered, and the like may be made by those skilled in the art in accordance with the principles set forth hereinabove and in the claims annexed hereto.

What is claimed is:

1. A method of treating pain in humans and warm-blooded animals, comprising the step of administering to said human or said warm-blooded animal a pharmaceutical composition having high analgesic activity and including an analgesic agent comprising a 5-phenyl-1H-2,3-dihydro-1,4-benzodiazepine compound of the following Formula I

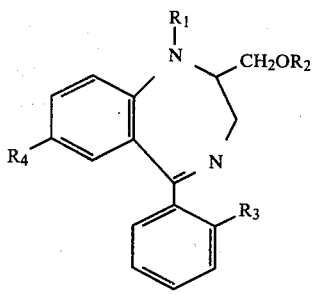

in which

R₁ represents a substituent selected from the group consisting of hydrogen and lower alkyl, R₂ represents a substituent selected from the group consisting of hydrogen, lower alkyl, and lower alkanoyl, R₃ represents a substituent selected from the group consisting of hydrogen and halogen, and R₄ represents halogen, or a physiologically compatible acid addition salt of said compounds together with pharmaceutical excipients and binding agents, in an analgesically effective amount sufficiently small so as not to cause any substantial sedative and muscle relaxing effects.

2. The method according to claim 1, wherein said composition comprises, as said analgesic agent, a compound of Formula I, in which R₁ represents lower alkyl.

3. The method according to claim 1, wherein said composition comprises, as said analgesic agent, a compound of Formula I, in which R₄ represents a halogen substituent selected from the group consisting of chlorine and bromine.

4. The method according to claim 1, wherein said composition comprises, as said analgesic agent, a compound of Formula I, in which R₂ represents lower alkyl.

5. The method according to claim 1, wherein said composition comprises, as said analgesic agent, a compound of Formula I, in which R₁ represents a substituent selected from the group consisting of hydrogen and methyl, R₂ represents a substituent selected from the group consisting of hydrogen and lower alkyl with 1 to 3 carbon atoms, R₃ represents halogen, and R₄ represents a substituent selected from the group consisting of chlorine and bromine.

6. The method according to claim 1, wherein said composition comprises, as said analgesic agent, a compound of Formula I, in which R₁ and R₂ each represent methyl, R₃ represents chlorine, and R₄ represents bromine.

7. The method according to claim 1, wherein said composition comprises, as said analgesic agent, a compound of Formula I, in which R₁ and R₂ each represent methyl, and R₃ and R₄ each represent chlorine.

8. The method according to claim 1 comprising administering to humans and warm-blooded animals an amount of between about 0.25 mg and about 25 mg of said compound of Formula I as a single analgesic dosage, said dosage being sufficiently low so as not to cause any substantial sedative and muscle relaxing effects.

* * * * *